United States Patent
Farone et al.

(10) Patent No.: US 6,439,034 B1
(45) Date of Patent: Aug. 27, 2002

(54) ACOUSTIC VISCOMETER AND METHOD OF DETERMINING KINEMATIC VISCOSITY AND INTRINSIC VISCOSITY BY PROPAGATION OF SHEAR WAVES

(75) Inventors: William A. Farone, Irvine; Robert F. Sacher, Costa Mesa; Charles Fleck, Woodland, all of CA (US)

(73) Assignee: Conagra Grocery Products Company, Irvine, CA (US)

( * ) Notice: Subject to any disclaimer, the term of this patent is extended or adjusted under 35 U.S.C. 154(b) by 0 days.

(21) Appl. No.: 09/699,949

(22) Filed: Oct. 30, 2000

(51) Int. Cl.[7] .................. G01N 11/14; G01N 09/32; G01N 11/02; G01F 17/00
(52) U.S. Cl. ............... 73/54.24; 73/648; 73/592
(58) Field of Search ............... 73/54.24, 54.27, 73/648, 592, 54.41

(56) References Cited

U.S. PATENT DOCUMENTS

| | | | |
|---|---|---|---|
| 2,490,452 A | * 12/1949 | Mason | 177/386 |
| 2,518,348 A | * 8/1950 | Mason | 73/54 |
| 2,707,391 A | * 5/1955 | McSkimin | 73/59 |
| 3,903,732 A | * 9/1975 | Rork | 73/54 |
| 4,331,025 A | 5/1982 | Ord, Jr. | 73/54 |
| 4,655,086 A | * 4/1987 | Mielnicka-Pate et al. | 73/646 |
| 4,799,378 A | * 1/1989 | Portman, Jr. et al. | 73/54 |
| 5,067,344 A | * 11/1991 | Fitzgerald et al. | 73/54 |
| 5,302,878 A | * 4/1994 | Soucemarianadin et al. | 310/360 |
| 5,303,578 A | * 4/1994 | Williams et al. | 73/54.24 |
| 5,365,778 A | 11/1994 | Sheen et al. | 73/54.41 |
| 5,768,937 A | * 6/1998 | Wajid et al. | 73/24.06 |
| 5,825,119 A | * 10/1998 | Shibata et al. | 310/338 |
| 5,837,885 A | * 11/1998 | Goodbread, et al. | 73/32 A |
| 6,260,408 B1 | * 7/2001 | Vig et al. | 73/64.53 |

OTHER PUBLICATIONS

A.B. Bhatia; "Classical Causes of Absorption with Application of Monatomic Fluids," *Ultrasonic Absorption*, 1985, pp. 55–56, Chp 4, Dover Publiczations, Inc., New York.
Philip M. Morse et al., "Acoustic Wave Motion, Ch 6.4 Internal Energy Loss," *Theoretical Acoustics*, 1986 pp. 274–291; Princeton University Press, Princeton, New Jersey.

* cited by examiner

Primary Examiner—Hezron Williams
Assistant Examiner—David J. Wiggins
(74) Attorney, Agent, or Firm—Christie, Parker & Hale, LLP

(57) ABSTRACT

An acoustic viscometer and method for determining both the kinematic viscosity and the intrinsic viscosity of a liquid which includes an acoustic wave generator, a transmitting piezoelectric transducer, a receiving piezoelectric transducer, and a phase-shift detector. The transmitting piezoelectric transducer is positioned so as to be in contact with the liquid and is operably connected to the acoustic wave generator. The transmitting piezoelectric transducer propagates a longitudinal wave of known frequency through the liquid. The receiving piezoelectric transducer is spaced apart from the transmitting piezoelectric transducer and detects the longitudinal wave and a corresponding shear wave propagated through the liquid. The phase-shift detector is operably connected to both the transmitting and receiving piezoelectric transducers and measures the difference in phase between the longitudinal wave propagated by the transmitting piezoelectric transducer and the longitudinal and shear wave detected by the receiving piezoelectric transducer. The difference in phase is used to determine the velocity of the shear wave, and the kinematic and intrinsic viscosities of the liquid in terms of liquid density.

23 Claims, 9 Drawing Sheets

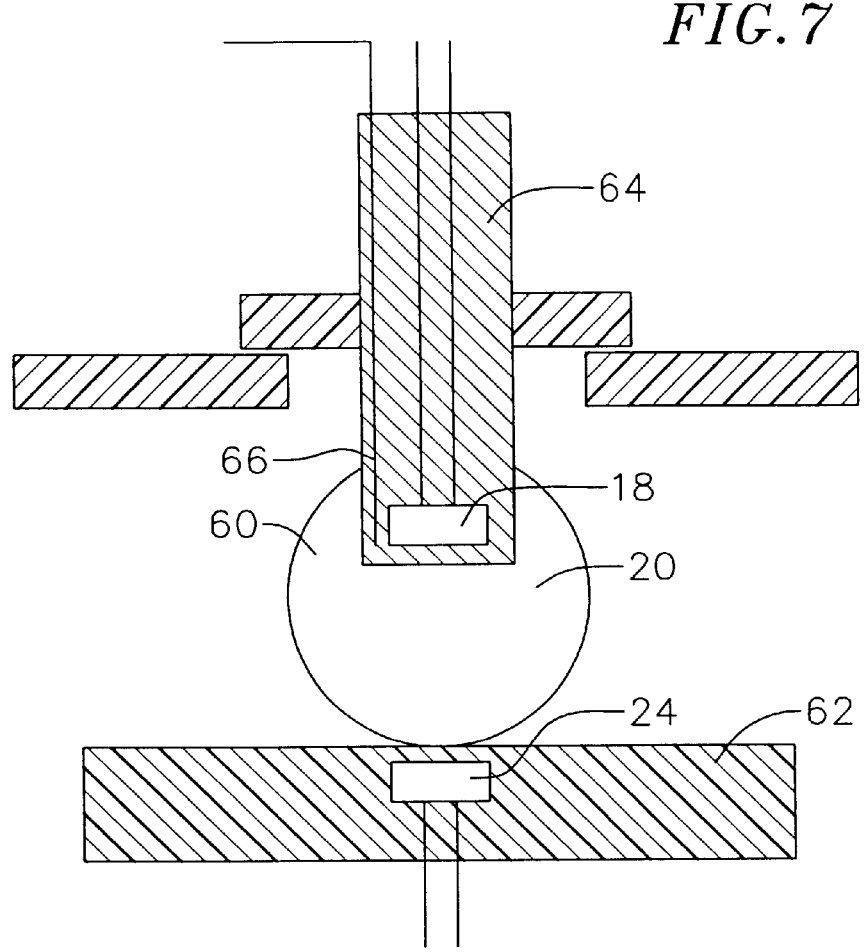
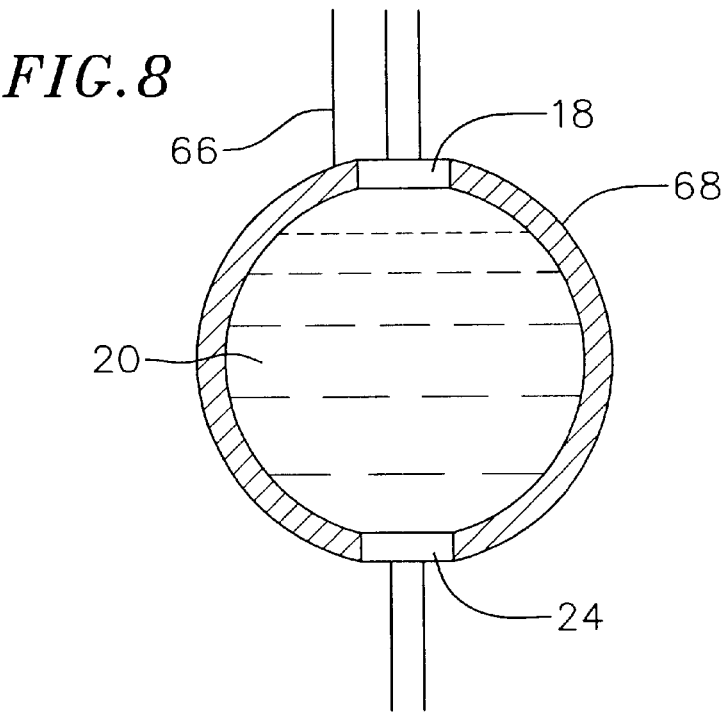

ACOUSTIC VISCOMETER AND METHOD OF DETERMINING KINEMATIC VISCOSITY AND INTRINSIC VISCOSITY BY PROPAGATION OF SHEAR WAVES

BACKGROUND OF THE INVENTION

1. Field of the Invention

The present invention relates generally to the measurement of viscosity of liquids, and in particular to electronic devices and methods which measure kinematic viscosity.

2. Background

Determining intrinsic viscosity and kinematic viscosity is a fundamental requirement to properly carry out many industrial and manufacturing processes, including food preparation. Generally, intrinsic viscosity is defined as the internal resistance to flow exhibited by a liquid. A liquid has an intrinsic viscosity of one poise if a force of one dyne per square centimeter causes two parallel liquid surfaces one square centimeter in area and one centimeter apart to move past one another at a velocity of one centimeter per second. Kinematic viscosity is equal to intrinsic viscosity divided by the density of the liquid, where both the intrinsic viscosity and density of the liquid are measured at the same temperature.

It is known that certain properties of liquids are related to the velocity of waveforms traveling through those liquids. One type of waveform is a longitudinal, or compressional wave. When an acoustic longitudinal wave travels through a liquid, the liquid molecules vibrate in the same direction as that in which the longitudinal wave is propagated. At certain frequencies of longitudinal waves, another type of waveform called a shear wave is also propagated in liquids. When a shear wave travels through a liquid, the molecules of the liquid vibrate in a direction transverse to the direction of propagation of the longitudinal wave. The vibration of the molecules induced by the shear wave is coupled to the natural frequencies of vibration of the liquid. As explained by A. B. Bhatia, *Ultrasonic Absorption*, Dover Publications, 1967, if the velocity of a shear wave is measured, the kinematic viscosity can be directly calculated, and furthermore, if the density of the liquid is also known, the intrinsic viscosity can be easily calculated.

Several known devices employ acoustic waves to measure the density of a liquid and use the density measurement to calculate or approximate the kinematic viscosity and intrinsic viscosity. These devices use acoustic waves to measure density, but do not directly measure the intrinsic viscosity or kinematic viscosity of a liquid.

One such device, described in U.S. Pat. No. 4,331,025, tries to measure the flow rate of a liquid by determining the velocity of a longitudinal wave propagated in the liquid based on the velocity of an acoustic transmission from an upstream location to a downstream location, and also from the downstream location to the upstream location. It then uses the temperature of the liquid and certain predetermined constants to calculate the kinematic viscosity of the liquid. This device and method measures the velocity of the longitudinal wave rather than the velocity of the corresponding shear wave. A disadvantage of this approach to the problem is that calculated empirical constants used to determine the kinematic viscosity of the liquid are dependent on the type of liquid to be measured. Thus, the ability to use this method on a wide variety of liquids is limited by the need to calculate the constants for each liquid prior to the use of the method and device on a new liquid.

Another device, described in U.S. Pat. No. 5,365,778, attempts to determine the intrinsic viscosity of the liquid in response to both longitudinal waves and shear waves. A disadvantage of this device is that, to perform the necessary calculations to determine kinematic viscosity, the device must measure the velocity of both shear wave and longitudinal waves, thus requiring multiple measuring transducers and additional data calculating elements.

Yet another device, disclosed in U.S. Pat. No. 3,903,732, attempts to determine liquid intrinsic viscosity and density by measuring the effective input impedance on a single transducer as a function of the liquid's reactive dampening force. A disadvantage of this device is that it yields only the intrinsic viscosity and the density of the liquid, not the kinematic viscosity. A further disadvantage is hat six constants need to be calculated prior to using the device on the liquid of interest.

A difficulty encountered with some devices that use acoustic wave measurements when calculating kinematic viscosity and intrinsic viscosity is that they operate at frequencies above 1 MHz. At these high frequencies, the shear wave is not properly established due to the short transient time between the maxima and minima in the, waveform. Furthermore, at these. frequencies shear waves, which are highly attenuated, degenerate rapidly over a very short distance, thus making them difficult to detect. This prevents effective measurement of the shear wave velocity and use of shear waves to determine intrinsic viscosity and kinematic viscosity. As a result, a great deal of energy is required to propagate the shear wave for even short distances in a liquid, thus creating serious difficulties in efficiently measuring the velocity of the shear wave in industrial applications. A further problem is that the change of the liquid in reaction to a shear wave is a transient phenomena characterized by the relaxation time of the molecules as they respond to a wave. Consequently, it is desired that the acoustic wave be such that the relaxation time for the molecules in the liquid is long enough to significantly cause and maintain the shear wave.

In view of the above, it should be appreciated that there is a need for a device and method for determining the intrinsic viscosity and kinematic viscosity of a liquid which can be used with a variety of liquids without precalculation of constants. There is also a need for such a device that is capable of creating and maintaining a shear wave in a liquid and is capable/of measuring shear waves over an extended distance. There is a need for such a device to be able to measure shifts of shear wave velocity independent of shear wave amplitude. There is a further need for the device to have low power requirements and/or operate at a low frequency. The present invention satisfies these and other needs and provides further related advantages.

SUMMARY OF THE INVENTION

The present invention resides in a device and method for determining the intrinsic viscosity and kinematic viscosity of a liquid which can be used on a variety of liquids without precalculation of constants. It is capable of creating and maintaining a shear wave in a liquid and is capable of measuring shear waves over an extended distance. It also can measure shifts of shear wave velocity independent of shear wave amplitude. It has low power requirements and/or operates at a low frequency.

The acoustic viscometer can include an acoustic wave generator, a transmitting piezoelectric transducer, a receiving piezoelectric transducer, and a phase-shift detector. The acoustic wave generator and transmitting piezoelectric transducer, which is positioned so as to be in contact with a liquid, are operably connected to each other. The transmitting piezoelectric transducer can propagate a longitudinal wave through the liquid. The longitudinal wave and a corresponding shear wave can be detected by a receiving piezoelectric transducer, which is advantageously spaced-apart from the transmitting piezoelectric transducer, and is operably connected to a phase-shift detector. The phase-shift detector is also operably connected to the transmitting piezoelectric transducer. The phase-shift detector measures the difference in phase between the longitudinal wave propagated by the transmitting piezoelectric transducer and the longitudinal and shear wave detected by the receiving piezoelectric transducer. The difference in phase can be used to determine the velocity of the shear wave, and the kinematic and intrinsic viscosities of the liquid.

Some embodiments of the invention include a transmitting piezoelectric transducer which can propagate a shear wave in a liquid over a distance of at least about one inch. The transmitting piezoelectric transducer can be driven by a voltage of at least about ninety volts, and the transmitting piezoelectric transducer and/or the receiving piezoelectric transducer can have a coating which may have a thickness of less than 0.1 millimeter.

This invention can be used to determine the difference in phase between the longitudinal wave propagated by the transmitting piezoelectric transducer and the longitudinal and shear wave detected by the receiving piezoelectric transducer. This can be accomplished regardless of each wave's amplitude.

In some embodiments of the invention, the transmitting piezoelectric transducer can propagate a shear wave with a frequency ranging between about 20 kHz and about 100 kHz. This advantageously allows the shear wave to be properly established. Some embodiments include a temperature sensor for measuring the temperature of the liquid. The acoustic wave generator may be a pulse generator or a crystal oscillator, and the acoustic viscometer may be battery powered.

The invention can include a phase-to-voltage convector connected to the phase-shift detector to convert the difference in phase between the longitudinal wave propagated by the transmitting piezoelectric transducer and the longitudinal and shear wave received by the receiving piezoelectric transducer to a voltage. An output device can connect to the phase-to-voltage convector and display a value corresponding to the voltage.

The method of the present invention may include placing the transmitting and receiving piezoelectric transducers in contact with the liquid. A longitudinal wave and a corresponding shear wave are propagated by vibrating the transmitting piezoelectric transducer. The receiving piezoelectric transducer detects the longitudinal and shear wave. The method also involves determining the difference in phase between the longitudinal wave propagated by the transmitting piezoelectric transducer and the longitudinal and shear wave detected by the receiving piezoelectric transducer, determining the velocity of the shear wave, and determining the kinematic and intrinsic viscosities of the liquid.

The methods of the present invention may also include allowing at least about one inch of spacing between the transmitting and receiving piezoelectric transducers, determining the difference in phase between the longitudinal wave propagated by the transmitting piezoelectric transducer and the longitudinal and shear wave detected by the receiving piezoelectric transducer regardless of wave amplitude, the transmitting piezoelectric transducer propagating a shear wave with a frequency between about 20 kHz to about 100 kHz, and determining the temperature of the liquid. The method may include liquid flowing past the transmitting and receiving piezoelectric transducers, and liquid located within a piece of fruit. Still other methods include converting the difference in phase between the longitudinal wave propagated by the transmitting piezoelectric transducer and the longitudinal and shear wave detected by the receiving piezoelectric transducer to a voltage, and transmitting the voltage to an output device for displaying a value that corresponds to the voltage.

One advantage of the invention is that it can provide a measurable shear wave for determining the intrinsic viscosity and the kinematic viscosity of a liquid. Thus, the acoustic viscometer provides an accurate measurement of the kinematic viscosity without any prior measurements of constants related to the subject liquid. An advantage of the invention is that it detects the phase shift of a shear wave without regard to attenuation of the shear wave, increasing the accuracy of the acoustic viscometer.

Other features and advantages of the present invention will be set forth in the description which follows and the accompanying drawings, wherein the preferred embodiments of the present invention are described and shown, and will become apparent to those skilled in the art upon examination of the following detailed description taken in conjunction with the accompanying drawings, may be learned by practice of the present invention.

BRIEF DESCRIPTION OF THE DRAWINGS

FIG. 7 is a schematic diagram of an acoustic viscometer interfacing a piece of fruit.

FIG. 8 is a sectional view of an acoustic viscometer with a transmitting piezoelectric transducer and a receiving piezoelectric transducer mounted on opposing sides of a pipe.

DESCRIPTION OF THE PREFERRED EMBODIMENTS

Figure 1:
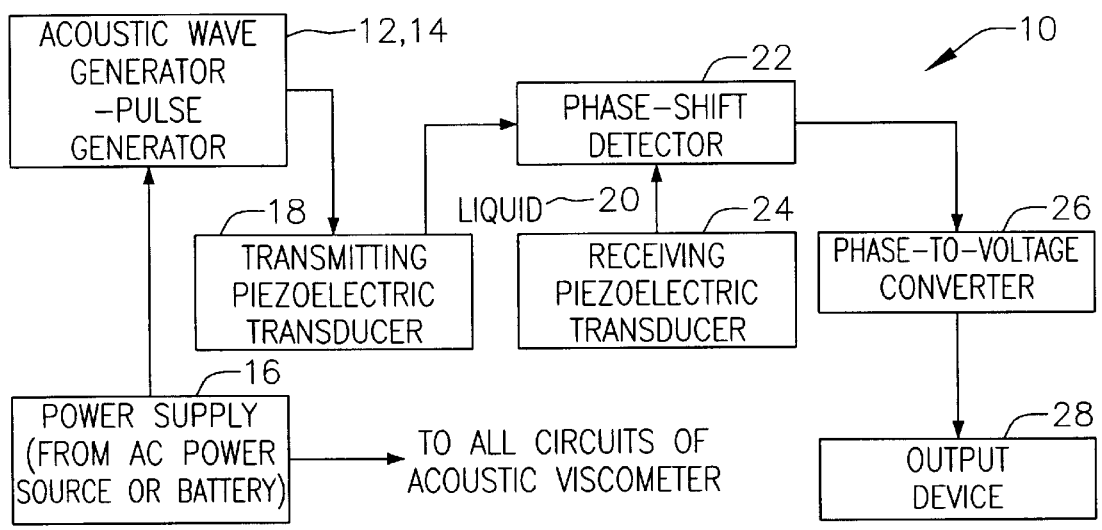
FIG. 1 is a schematic block diagram of an acoustic viscometer in accordance with the present invention.

With reference to FIG. 1, the acoustic viscometer 10 of the present invention includes an acoustic wave generator 12 in the form of a pulse generator 14. The pulse generator is operably connected to a power supply 16 and to a transmitting piezoelectric transducer 18 in contact with a liquid 20. The transmitting piezoelectric transducer is also operatively connected to aphase-shift detector 22.

The phase-shift detector 22 is connected to receive signals from a receiving piezoelectric transducer 24. The receiving piezoelectric transducer is spaced from the transmitting piezoelectric transducer 18 and is in contact with the liquid 20. The phase-shift detector is operatively connected to a phase-to-voltage converter 26, which in turn is operatively connected to an output device 28.

In operation, the pulse generator 14 converts the power provided by the power supply 16 into voltage pulses which then drive the transmitting piezoelectric transducer 18 to vibrate and propagate a longitudinal wave in the liquid 20. The receiving piezoelectric transducer 24 detects the longitudinal wave and a corresponding shear wave. The phase-shift detector 22 measures the difference in phase between the longitudinal wave propagated by the transmitting piezoelectric transducer and the longitudinal and shear wave detected by the receiving piezoelectric transducer. The phase-to-voltage converter 26 converts the difference in phase to a voltage value which is displayed on the output device 28. Additionally, the acoustic viscometer 10 calculates the velocity of the shear wave based on the difference in phase. Based on the measurement of the shear wave velocity, the kinematic viscosity ($\eta/\rho$) can be determined:

$$\frac{\eta}{\rho} = \frac{V^2}{2\omega}$$

where:

V is the velocity of the shear wave, $\omega$ is $2\pi$ times-the frequency of the shear wave, $\eta$ is the intrinsic viscosity of the liquid, and $\rho$ is the density of the liquid.

Therefore, the kinematic viscosity of the liquid can be determined if the velocity of the shear wave is accurately measured, and the frequency of the shear wave is known. Also, the intrinsic viscosity of the liquid may be determined if the kinematic viscosity and the density of the liquid are known. It is important to note that both the intrinsic viscosity and density of a liquid are a function of temperature. Also, the acoustic viscometer may be periodically calibrated by testing the velocity of a known liquid, such as water, to ensure consistent and accurate results.

To properly establish the shear wave in the liquid 20 over an appropriate distance, at least about one inch, between the transmitting and receiving piezoelectric transducers 18 and 24, the driving voltage of the transmitting piezoelectric transducer is preferably about 90 volts or more, and advantageously may be as high as about 300 volts. Several commercially available piezoelectric transducers designed to transmit and receive an acoustic signal in air meet this voltage requirement. Examples include the Mouser Electronics ME251-1603, available from the Mouser Electronics Company and the Polaroid Corporation Instrument Grade Electrostatic Transducer Part Number 604142, available from the Polaroid Corporation. It is of course understood that other commercial piezoelectric transducers may exist or be developed, and the examples given do not limit the scope of acceptable choices.

Figure 2:
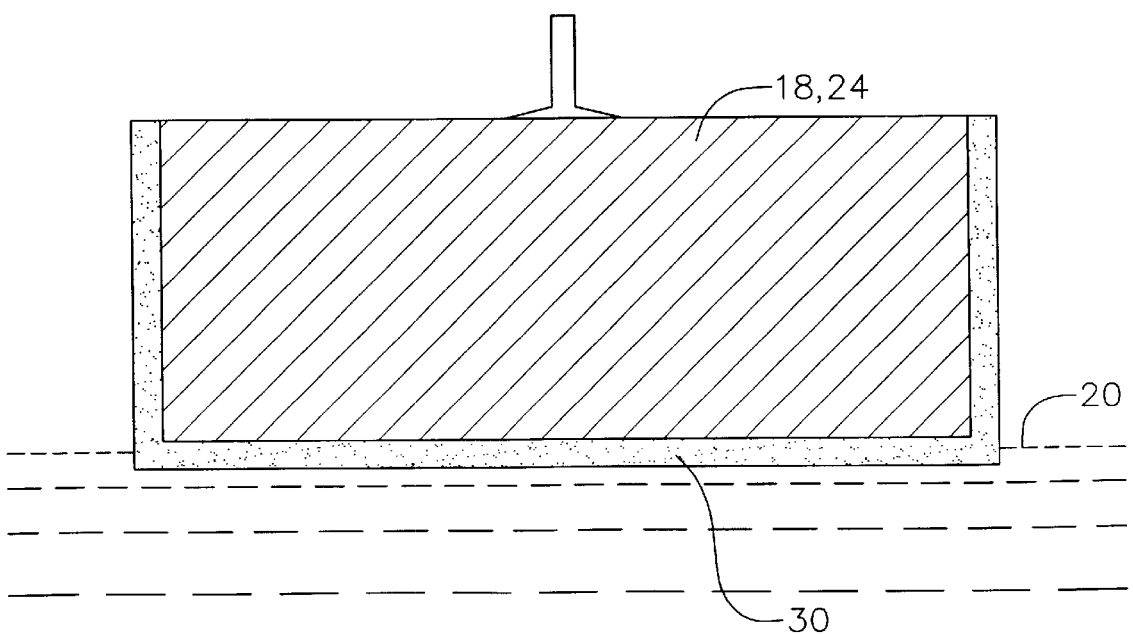
FIG. 2 is a sectional view of a piezoelectric transducer with a coating.
Figure 3A:
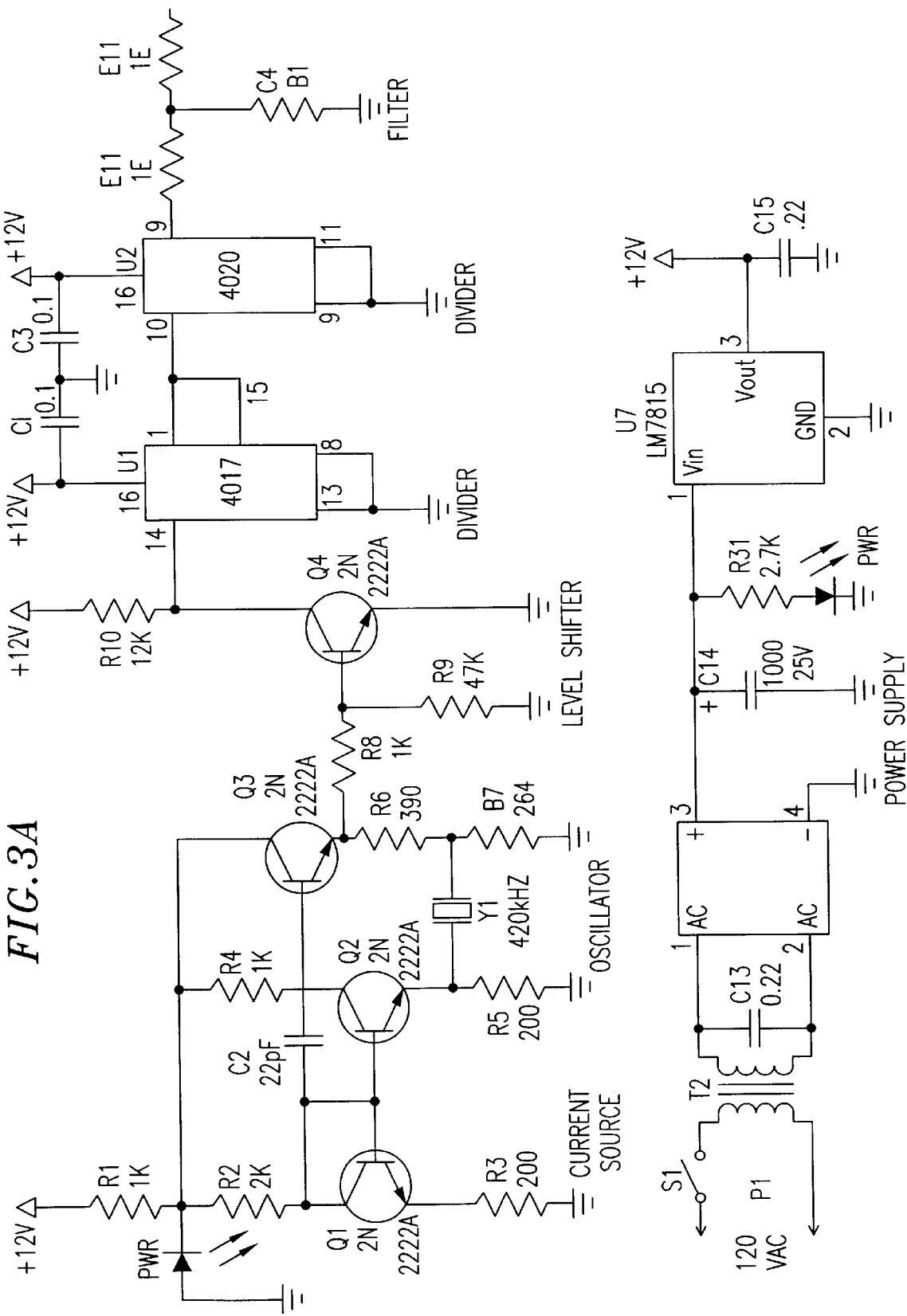
FIGS. 3A and 3B are circuit diagrams corresponding to portions of the schematic block diagram of FIG. 1.
Figure 3B:
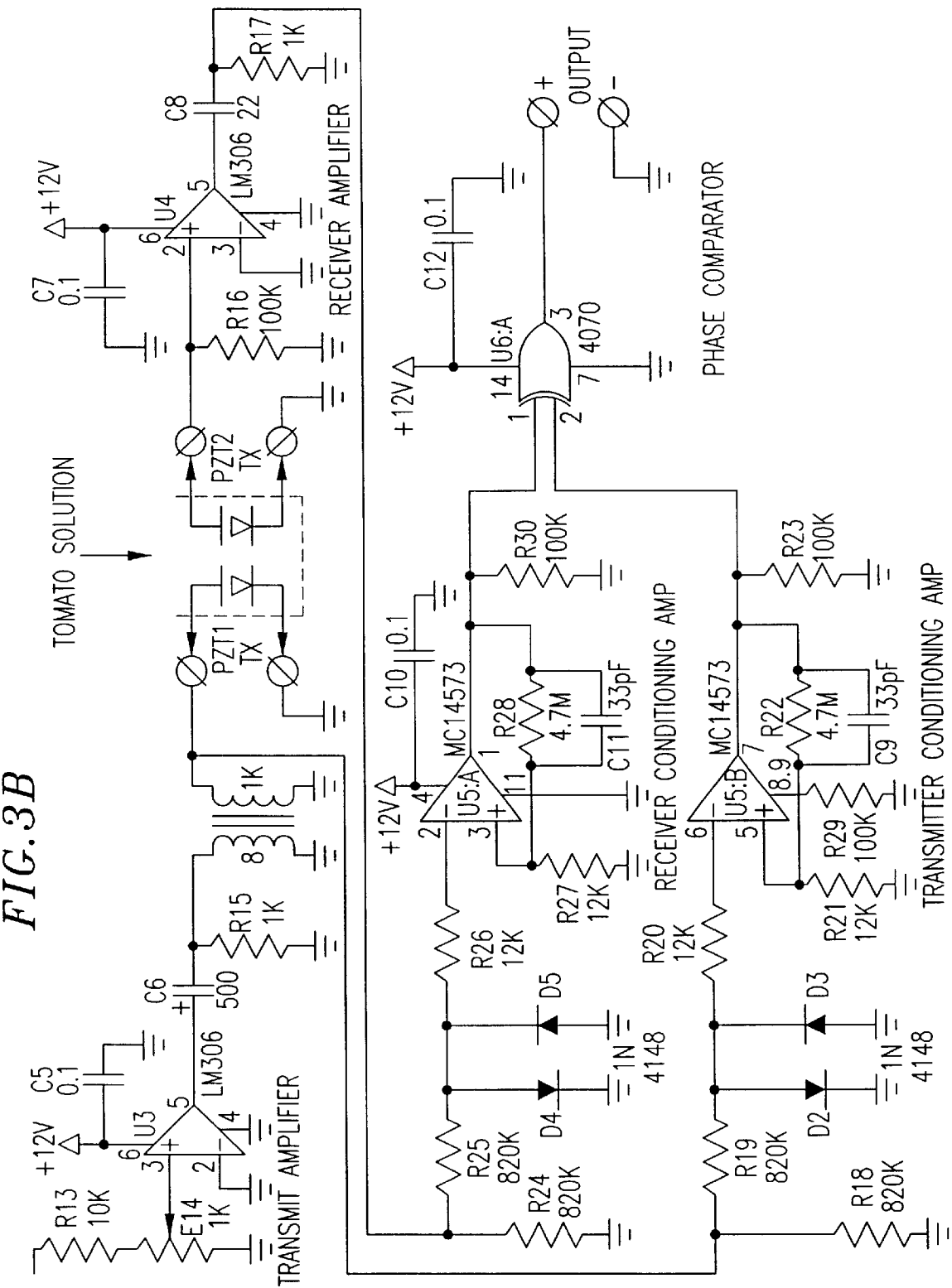
Figure 4A:
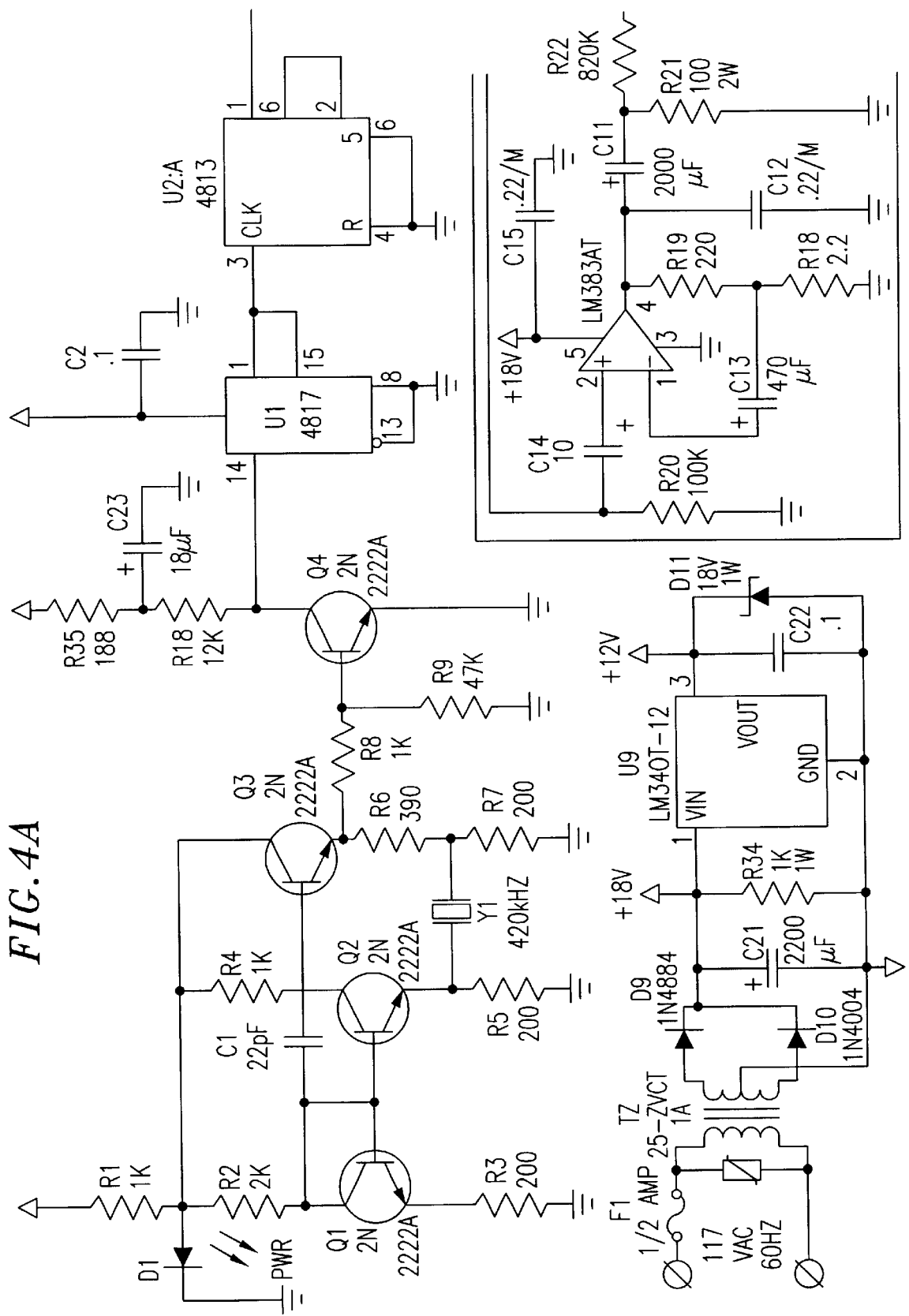
FIGS. 4A, 4B, and 4C are diagrams of alternative circuits corresponding to portions of the schematic block diagram of FIG. 1.
Figure 4B:
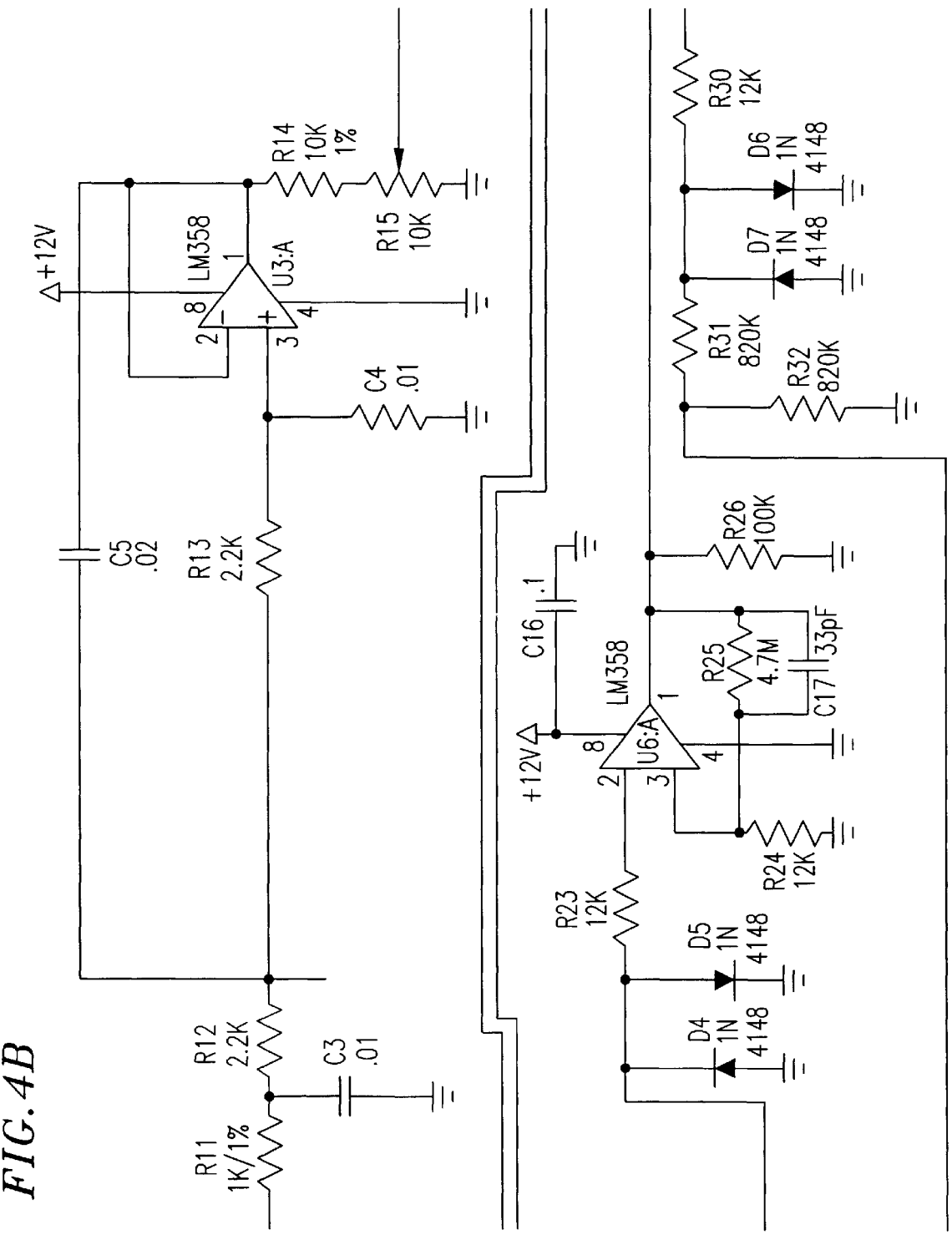
Figure 4C:
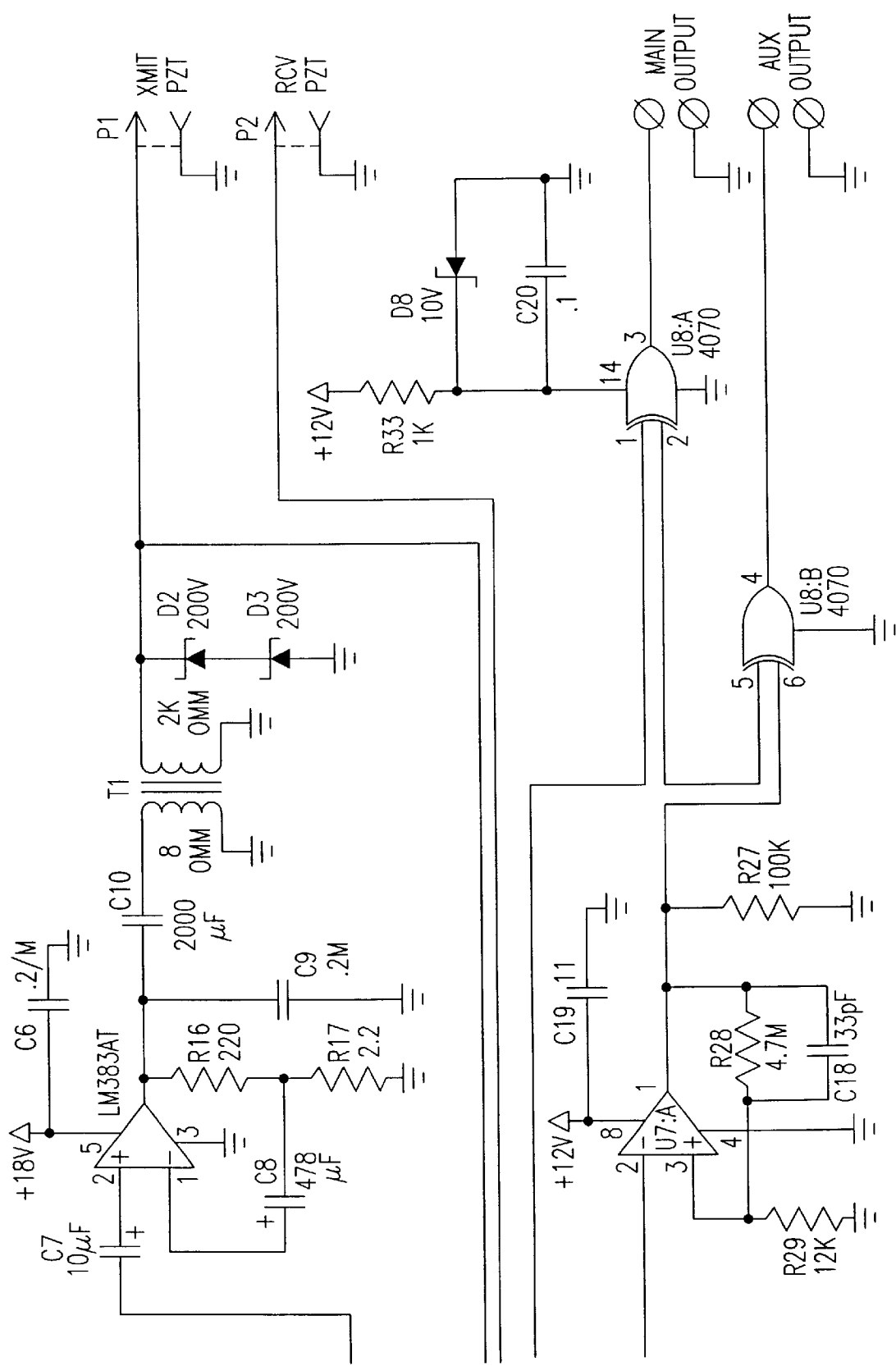

To enable the transmitting and receiving piezoelectric transducers 18 and 24 to be placed in effective contact with a reactive liquid (not shown), the piezoelectric transducers are preferably configured to be devoid of extraneous metallic parts. Many exposed metals can corrode and contaminate reactive samples. Referring to FIG. 2, the portions of the piezoelectric transducer that contact the liquid 20 also have a coating 30 that allows for the transmission of acoustic waves and isolates the piezoelectric transducer from the test liquid without reacting with or being degraded by the liquid. The coating may be made of epoxy. Protected by the coating, a piezoelectric transducer may be placed in contact with the liquid, or even fully immersed in the liquid without adversely affecting the piezoelectric transducer or contaminating the liquid. As previously noted, shear waves traveling through liquid are often rapidly attenuated. To maintain the ability of the receiving piezoelectric transducer to detect this attenuated wave, it is preferred that the thickness of the coating be minimized. Preferably, the coating has at thickness of less than 0.1 millimeter in most situations.

Returning to FIG. 1, the transmitting and receiving piezoelectric transducers 18 and 24, in combination with the pulse generator 14, propagate and measure shear waves with frequencies below 1 MHz. As previously explained, shear waves exhibit a transient phenomena characterized by a relaxation time of the molecules of the liquid 20 to be measured as they respond to the transmitted longitudinal wave. The relaxation time causes the difference in phase between the longitudinal wave propagated by the transmitting piezoelectric transducer and the longitudinal and shear wave detected by the receiving piezoelectric transducer, i.e., the change in velocity that is related to the molecular structure of the liquid. However, it has been found that at frequencies below 1 MHz the relaxation times are sufficiently great to establish distinquishable shear waves. At frequencies of 1 MHz and above, the difference in phase between the transmitted longitudinal wave and the received longitudinal and shear wave is a much smaller percentage of the frequency and harder to measure and establish in the liquid. Preferably, the transmitting piezoelectric transducer propagates a shear wave with a frequency between about 20 kHz and about 100 kHz, with best results for most liquids obtained in the frequency range of about 36 kHz to about 44 kHz.

FIGS. 3A and 3B, and 4A, 4B, and 4C are representative circuit diagrams for the power supply 16, pulse generator 14, phase-shift detector 22, and phase-to-voltage convector 26, shown as blocks in FIG. 1. It is understood that other circuits may be used to accomplish the functionality set forth in the FIG. 1 block diagram. Accordingly, the circuit diagram shown in FIGS. 3A and 3B, and 4A, 4B, and 4C are shown for illustrative purposes only and are not intended to be limiting.

Figure 5:
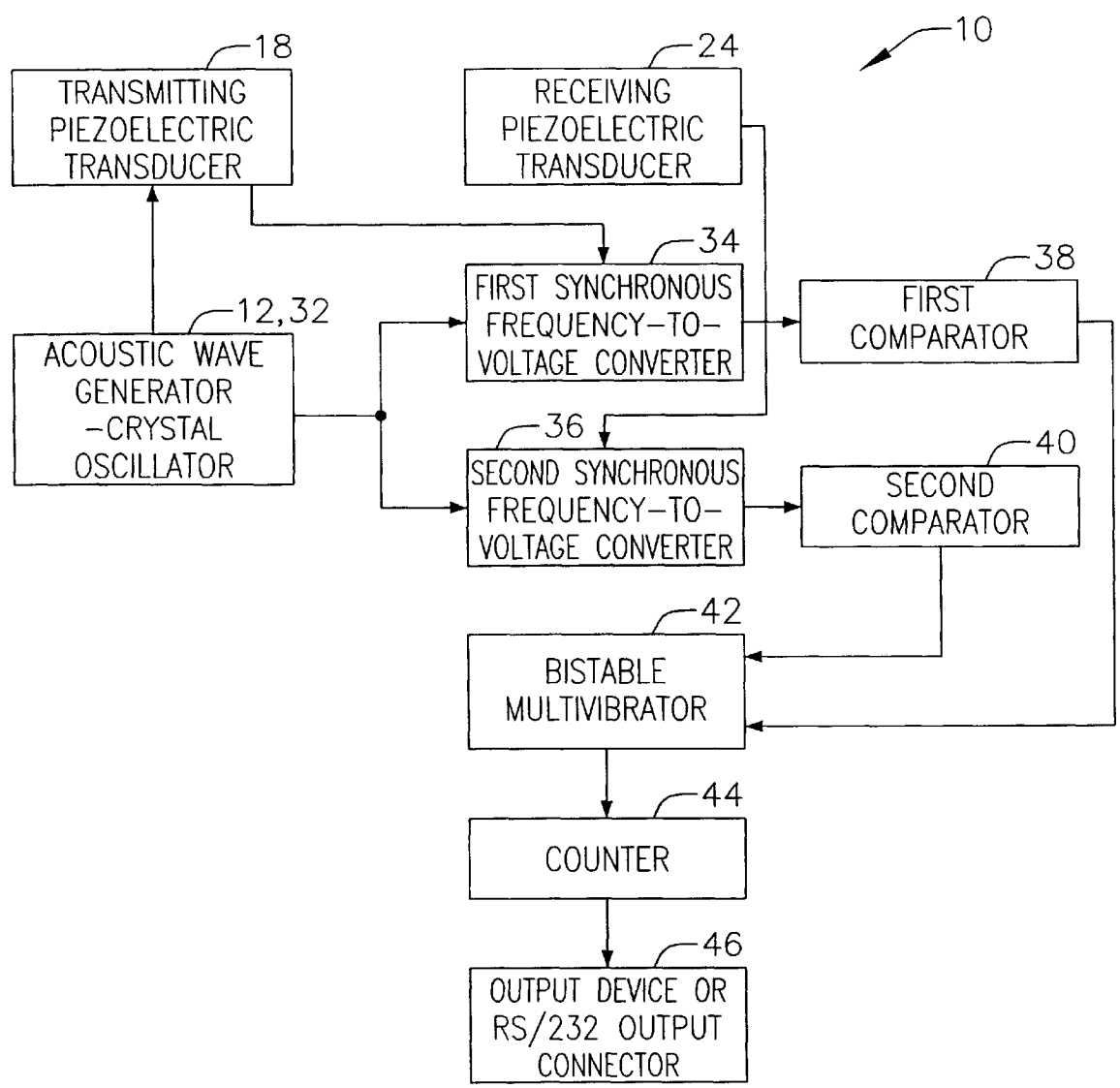
FIG. 5 is a schematic block diagram of an alternative embodiment of an acoustic viscometer in accordance with the invention.

The present invention can take the form of other embodiments. For example, another embodiment configured according to the present invention is shown in FIG. 5, which is a schematic block diagram of an alternative embodiment of the acoustic viscometer 10. Where appropriate, the same reference numbers are used to avoid unnecessary duplication and description of similar elements already referred to and described above. Only the significant differences between the second embodiment and the first embodiment will be discussed here.

In FIG. 5, the acoustic wave generator 12 is a crystal oscillator 32, which is operably connected to a transmitting piezoelectric transducer 18 and a first synchronous frequency-to-voltage convector 34. The transmitting piezoelectric transducer also is operably connected to the first synchronous frequency-to-voltage convector. Similarly, both the crystal oscillator and the receiving piezoelectric transducer 24 are operably connected to a second synchronous frequency-to-voltage convector 36. The first and second synchronous frequency-to-voltage convertors are operably connected to a first and second comparator 38 and 40, respectively. Both the first and second comparators are operably connected to a bistable multivibrator 42, which in turn is operably connected to a counter 44. The counter is operably connected to an output device or RS/232 output connector 46.

In operation, a waveform generated by the crystal oscillator 32 drives the transmitting piezoelectric transducer 18, which in turn propagates a longitudinal wave and an corresponding shear wave in a liquid (not shown). The waveform generated by the crystal oscillator is sent to both the first and second synchronous frequency-to-voltage convertors 34 and 36, respectively, which convert the frequency of the waveform into a voltage value. Additionally, the first and second synchronous frequency-to-voltage convertors, respectively, convert the frequencies of the longitudinal wave propagated by the transmitting piezoelectric transducer and the longitudinal and shear wave detected by the receiving piezoelectric transducer 24 into voltage values.

Next, the first comparator 38 compares the voltage values corresponding to the frequencies of the crystal oscillator 32 and the longitudinal wave propagated by the transmitting piezoelectric transducer 18. Similarly, the second comparator 40 compares the voltage values corresponding to the frequencies of the crystal oscillator and the longitudinal and shear wave detected by the receiving piezoelectric transducer 24. The output of the first comparator is logic level "high" when the voltage value corresponding to the frequency of the longitudinal wave propagated by the transmitting piezoelectric transducer is larger than the voltage value corresponding to the frequency of the crystal oscillator respectively. Likewise, the output of the second comparator is logic level "high" when the voltage value corresponding to the frequency of the longitudinal and shear wave detected by the receiving piezoelectric transducer is larger than the voltage value corresponding to the frequency of the crystal oscillator.

The output signals from the first and second comparators 38 and 40 are fed to a bistable multivibrator 42 which generates an output voltage signal which transitions, or "beats," between "high" and "low" logic levels more frequently when there is a greater difference in phase between the longitudinal wave propagated by the transmitting piezoelectric transducer 18 and the longitudinal and shear wave detected by the receiving piezoelectric transducer 24. A counter 44 counts the number of "beats" and sends the number to the output device or RS/232 output connector 46. The acoustic viscometer 10 thus uses the number of "beats" to calculate the shear wave's velocity, and determine the kinematic and intrinsic viscosities of the liquid.

Figure 6:
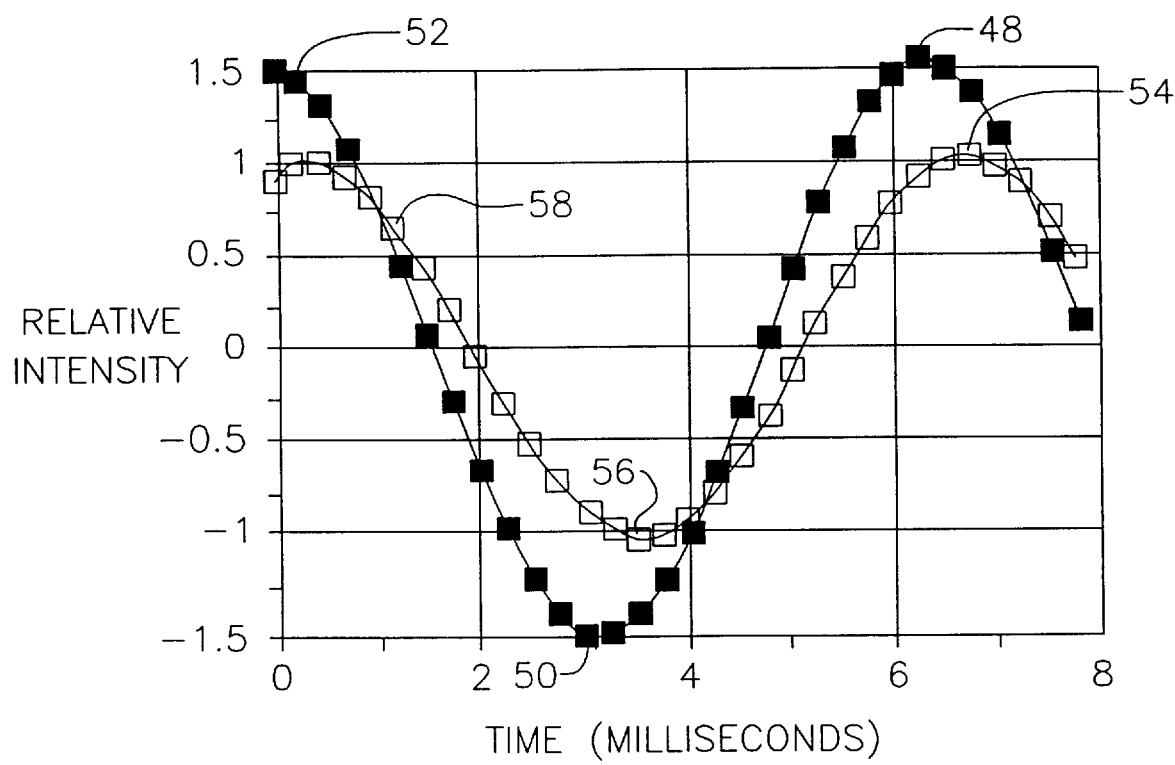
FIG. 6 is a graph illustrating the difference in phase between a longitudinal wave propagated by a transmitting piezoelectric transducer and a longitudinal and shear wave detected by a receiving piezoelectric transducer.

Referring to FIGS. 1 and 6, as the longitudinal and shear wave travels through the liquid 20, it slows down, and thus the wave has a lower velocity when it reaches the receiving piezoelectric transducer 24 than when the longitudinal wave left the transmitting piezoelectric transducer 18. The change in velocity is determined by measuring the phase shift between the maxima 48 and minima 50 of the longitudinal wave 52 propagated by the transmitting piezoelectric transducer and the maxima 54 and minima 56 the longitudinal and shear wave 58 detected by the receiving piezoelectric transducer as illustrated in FIG. 6. In practice, the amplitude difference between the transmitted longitudinal wave and the received longitudinal and shear wave is far greater than that shown and would render the graph difficult to use for purposes of explanation. Accordingly, this amplitude difference has been reduced for illustrative purposes.

In the alternative embodiment shown in FIG. 5, (see FIG. 6) the difference in phase between the longitudinal wave 52 propagated by the piezoelectric transducer 18 and the longitudinal and shear wave 58 detected by the receiving piezoelectric transducer 24 is determined by comparing the number of crystal oscillator 32 oscillation&;between successive maxima 48 and minima 50 of the transmitted longitudinal wave with the number of crystal oscillator oscillations between successive maxima 54 or minima 56 of the received longitudinal and shear wave. Therefore, the difference in phase is dependent upon the number of oscillations and independent of the amplitudes of the transmitted and received waveforms.

The components of the above described acoustic viscometer 10 may be mounted in various ways depending on the needs of the user, as will be apparent to those skilled in the art. For example, with reference to FIG. 7, a portable version of the acoustic viscometer for sampling the intrinsic viscosity of the liquid 20 within a piece of fruit 60 in the field can include a plastic base 62 and a penetrator 64. A receiving piezoelectric transducer 24 is contained within the plastic base. The penetrator includes a transmitting piezoelectric transducer 18 and a temperature sensor 66.

When in operation, a piece of fruit 60 is placed on the base 62. The penetrator 64 is lowered into the fruit such that the transmitting piezoelectric transducer 18 is at a predetermined, fixed, and known distance away from the receiving piezoelectric transducer 24. Preferably, this distance is at least about one inch. With this arrangement, difference in phase between the longitudinal wave propagated by the transmitting piezoelectric transducer and the longitudinal and shear wave detected by the receiving piezoelectric transducer are measured and the velocity of the shear wave is determined, thus, allowing for the determination of the intrinsic viscosity of the liquid 20 in the fruit. This embodiment of the invention also allows for measurement of the temperature of the liquid in the fruit. Referring additionally to FIG. 1, portability is readily achieved because the low wattage requirement of the device allows it to be powered by a battery power supply 16.

In another arrangement, shown in FIG. 8, the transmitting piezoelectric transducer 18 and receiving piezoelectric transducer 24, along with the temperature sensor 66, are permanently mounted on opposing sides of a pipe 68 through which a liquid 20 to be measured flows. In this arrangement, longitudinal waves travel perpendicular to the liquid flow path allowing the intrinsic viscosity and kinematic viscosity to be measured during real-time processing of the liquid. For accurate measurement, liquid flow should be kept at a low velocity enough so that no acoustic waves are induced in the liquid at frequencies near 40 kHz.

Those skilled in-the art will recognize that other modifications and variations can be made in the acoustic viscometer 10 and method of the present invention and in the construction and operation of the acoustic viscometer without departing from the scope and spirit of this invention. With such possibilities in mind, the invention is defined with reference to the following claims.

We claim:
1. An acoustic viscometer for determining both the kinematic viscosity and the intrinsic viscosity of a liquid comprising:
   an acoustic wave generator;
   a transmitting piezoelectric transducer operably connected to the acoustic wave generator and positioned so as to be in contact with the liquid so as to propagate a longitudinal wave of known frequency through the liquid;
   a receiving piezoelectric transducer, spaced apart from the transmitting piezoelectric transducer and in contact with liquid, so as to detect the longitudinal, wave and a corresponding shear wave propagated through the liquid in terms of liquid density; and
   a phase-shift detector operably connected to the transmitting piezoelectric transducer and the receiving piezo- electric transducer to measure a difference in phase between the longitudinal wave propagated by the transmitting piezoelectric transducer and the longitudinal and shear wave detected by the receiving piezoelectric transducer, the difference in phase used to determine the velocity of the shear wave, and the kinematic viscosity and the intrinsic viscosity of the liquid in terms of liquid density.

2. The acoustic viscometer of claim 1 wherein the transmitting piezoelectric transducer is capable of propagating the shear wave in the liquid over a distance of at least about one inch.

3. The acoustic viscometer of claim 1 wherein the transmitting piezoelectric transducer is driven by a voltage of at least about ninety volts.

4. The acoustic viscometer of claim 1 wherein the transmitting piezoelectric transducer is driven by a voltage of between about ninety and about three hundred volts.

5. The acoustic viscometer of claim 1 wherein the difference in phase between the longitudinal wave propagated by the transmitting piezoelectric transducer and the longitudinal and shear wave detected by the receiving piezoelectric transducer is determined without regard to the amplitudes of the longitudinal wave and the shear wave.

6. The acoustic viscometer of claim 1 wherein at least one of the transmitting piezoelectric transducer and the receiving piezoelectric transducer have a coating.

7. The acoustic viscometer of claim 6 wherein the coating has a thickness of less than 0.1 millimeter.

8. The acoustic viscometer of claim 1 wherein the transmitting piezoelectric transducer propagates the shear wave with a frequency between about 20 kHz and about 100 kHz.

9. The acoustic viscometer of claim 1 wherein the transmitting piezoelectric transducer propagates the shear wave with a frequency between about 36 kHz and about 44 kHz.

10. The acoustic viscometer of claim 1 further comprising a temperature sensor for measuring the temperature of the liquid.

11. The acoustic viscometer of claim 1 wherein the acoustic wave generator is a pulse generator.

12. The acoustic viscometer of claim 1 wherein the acoustic wave generator is a crystal oscillator.

13. The acoustic viscometer of claim 1 wherein the acoustic viscometer is battery powered.

14. The acoustic viscometer of claim 1 further comprising:
a phase-to-voltage convector operably connected to the phase-shift detector to convert the difference in phase between the longitudinal wave propagated by the transmitting piezoelectric transducer and the longitudinal and shear wave detected by the receiving piezoelectric transducer to a voltage; and an output device operably connected to the phase-to-voltage convector for displaying a value corresponding to the voltage.

15. A method for determining both the kinematic viscosity and the intrinsic viscosity of a liquid comprising:
placing a transmitting piezoelectric transducer and a receiving piezoelectric transducer in contact with the liquid;
propagating a longitudinal wave and a corresponding shear wave in the liquid by vibrating the transmitting piezoelectric transducer;
detecting the longitudinal and shear wave With the receiving piezoelectric transducer;
determining a difference in phase between the longitudinal wave propagated by the transmitting piezoelectric transducer and the longitudinal and shear wave detected by the receiving piezoelectric transducer; and
determining a velocity of the shear wave, and the kinematic viscosity and the intrinsic viscosity of the liquid in terms of liquid density.

16. The method of claim 15 wherein the transmitting piezoelectric transmitter and the receiving piezoelectric transducer are at least about one inch apart.

17. The method of claim 15 wherein the difference in phase between the longitudinal wave propagated by the transmitting piezoelectric transducer and the longitudinal and shear wave detected by the receiving piezoelectric transducer is determined without regard to the amplitudes of the longitudinal wave and shear wave.

18. The method of claim 15 wherein the transmitting piezoelectric transducer propagates the shear wave with a frequency between about 20 kHz and about 100 kHz.

19. The method of claim 15 wherein the transmitting piezoelectric transducer propagates the shear wave with a frequency between about 36 kHz and about 44 kHz.

20. The method of claim 15 further comprising determining the temperature of the liquid.

21. The method of claim 15 wherein the liquid flows past the transmitting piezoelectric transducer and the receiving piezoelectric transducer.

22. The method of claim 15 wherein the liquid is present within a piece of fruit.

23. The method of claim 15 further comprising:
converting the difference in phase between the longitudinal wave propagated by the transmitting piezoelectric transducer and the longitudinal and shear wave detected by the receiving piezoelectric transducer to a voltage; and
transmitting the voltage to an output device for displaying a value corresponding to the voltage.

* * * * *

UNITED STATES PATENT AND TRADEMARK OFFICE
CERTIFICATE OF CORRECTION

PATENT NO.   : 6,439,034 B1
DATED        : August 27, 2002
INVENTOR(S)  : William A. Farone et al.

It is certified that error appears in the above-identified patent and that said Letters Patent is hereby corrected as shown below:

<u>Title page,</u>
Item [73], Assignee, "Conagra" should read -- ConAgra --
Item [56], OTHER PUBLICATIONS, "Publiczations" should read -- Publications" --

<u>Column 2,</u>
Line 13, replace "hat" with -- that --
Line 21, delete the comma after "minima in the"
Line 22, delete the period after "these"
Line 44, replace "capable/of" with -- capable of --

<u>Column 3,</u>
Lines 40 and 45, replace "convector" with -- convertor --

<u>Column 4,</u>
Line 27, after "drawings," and before "may" insert -- and --
Line 65, replace "aphase-shift" with -- a phase-shift --

<u>Column 5,</u>
Line 29, replace "times-the" with -- times the --

<u>Column 6,</u>
Line 9, replace "at" with -- a --
Lines 36, 55, 57 and 60, replace "convector" with -- convertor --

<u>Column 7,</u>
Line 3, replace "an" with -- a --
Line 53, after "56" and before "the" insert -- of --
Line 61, delete the comma after "5"
Line 62, insert a comma after "6)"
Line 66, replace "oscillation&,between" with -- oscillations between --

<u>Column 8,</u>
Line 44, replace "in-the" with -- in the --
Line 63, delete both commas
Line 65, delete "in terms of liquid density"

UNITED STATES PATENT AND TRADEMARK OFFICE
CERTIFICATE OF CORRECTION

PATENT NO.   : 6,439,034 B1
DATED        : August 27, 2002
INVENTOR(S)  : William A. Farone et al.

It is certified that error appears in the above-identified patent and that said Letters Patent is hereby corrected as shown below:

<u>Column 9,</u>
Line 47, replace "convector" with -- converter --

<u>Column 10,</u>
Line 2, replace "convector" with -- converter --
Line 12, "With" should read -- with --

Signed and Sealed this

Eleventh Day of March, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,439,034 B1
DATED         : August 27, 2002
INVENTOR(S)   : William A. Farone et al.

It is certified that error appears in the above-identified patent and that said Letters Patent is hereby corrected as shown below:

<u>Title page,</u>
Item [73], Assignee, "Conagra" should read -- ConAgra --
Item [56], OTHER PUBLICATIONS, "Publiczations" should read -- Publications" --

<u>Column 2,</u>
Line 13, replace "hat" with -- that --
Line 21, delete the comma after "minima in the"
Line 22, delete the period after "these"
Line 44, replace "capable/of" with -- capable of --

<u>Column 3,</u>
Lines 40 and 45, replace "convector" with -- convertor --

<u>Column 4,</u>
Line 27, after "drawings," and before "may" insert -- and --
Line 65, replace "aphase-shift" with -- a phase-shift --

<u>Column 5,</u>
Line 29, replace "times-the" with -- times the --

<u>Column 6,</u>
Line 9, replace "at" with -- a --
Lines 36, 55, 57 and 60, replace "convector" with -- convertor --

<u>Column 7,</u>
Line 3, replace "an" with -- a --
Line 53, after "56" and before "the" insert -- of --
Line 61, delete the comma after "5"
Line 62, insert a comma after "6)"
Line 66, replace "oscillation&,between" with -- oscillations between --

<u>Column 8,</u>
Line 44, replace "in-the" with -- in the --
Line 63, delete both commas
Line 65, delete "in terms of liquid density"

UNITED STATES PATENT AND TRADEMARK OFFICE
CERTIFICATE OF CORRECTION

PATENT NO. : 6,439,034 B1
DATED : August 27, 2002
INVENTOR(S) : William A. Farone et al.

It is certified that error appears in the above-identified patent and that said Letters Patent is hereby corrected as shown below:

Column 9,
Line 47, "convector" should read -- converter --

Column 10,
Line 2, "convector" should read -- converter --
Line 12, "With" should read -- with --

Signed and Sealed this

First Day of April, 2003

JAMES E. ROGAN
*Director of the United States Patent and Trademark Office*